US00PP18292P3

(12) United States Plant Patent

Trigiano et al.

(10) Patent No.: US PP18,292 P3

(45) Date of Patent: Dec. 11, 2007

(54) DOGWOOD TREE NAMED 'MISSY'S APPALACHIAN MORNING'

(50) Latin Name: ***Cornus florida* L.**
Varietal Denomination: Missy's Appalachian Morning

(75) Inventors: Robert N. Trigiano, Knoxville, TN (US); Mark T. Windham, Knoxville, TN (US); Alan S. Windham, Murfreesboro, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 5 days.

(21) Appl. No.: 11/315,886

(22) Filed: Dec. 22, 2005

(65) Prior Publication Data

US 2007/0150992 P1 Jun. 28, 2007

(51) Int. Cl.
*A01H 5/00* (2006.01)

(52) U.S. Cl. ..... Plt./220

(58) Field of Classification Search ..... Plt./220
See application file for complete search history.

(56) References Cited

U.S. PATENT DOCUMENTS

PP13,098 P2 10/2002 Windham et al.
PP13,099 P2 10/2002 Windham et al.
PP13,165 P2 11/2002 Windham et al.

*Primary Examiner*—Kent Bell
(74) *Attorney, Agent, or Firm*—Saliwanchik, Lloyd & Saliwanchik

(57) ABSTRACT

A new distinct cultivar of dogwood, *Cornus florida* L., named 'Missy's Appalachian Morning', is provided. This cultivar is characterized by producing fruit with seeds that will not germinate after industry standard cold/moist stratification for 4 months.

2 Drawing Sheets

BACKGROUND OF THE INVENTION

The present invention relates to a new and distinct cultivar of flowering dogwood, which produces fruit with seed(s) that fail to germinate after industry standard cold stratification procedures. This dogwood is botanically known as *Cornus florida* L. and hereinafter referred to by the following cultivar name: 'Missy's Appalachian Morning'.

This new dogwood cultivar was discovered growing in the landscape at the University of Tennessee in Knoxville, Tenn. in 1998. 'Missy's Appalachian Morning' is a white flowering dogwood possessing good horticultural traits including inflorescences subtended with square, overlapping white bracts. It is unique in that the seeds produced by sexual reproduction will not germinate following cold/moist stratification for four (4) months, which is the standard in the nursery industry. Asexual reproduction of 'Missy's Appalachian Morning' by terminal cuttings harvested at the Tennessee Agricultural Experiment Station in Knoxville, Tenn. and grafting of axillary buds onto seedling rootstocks have shown that the unique features of this new dogwood cultivar are stable.

DETAILED DESCRIPTION OF THE NEW VARIETY

Figure 1:
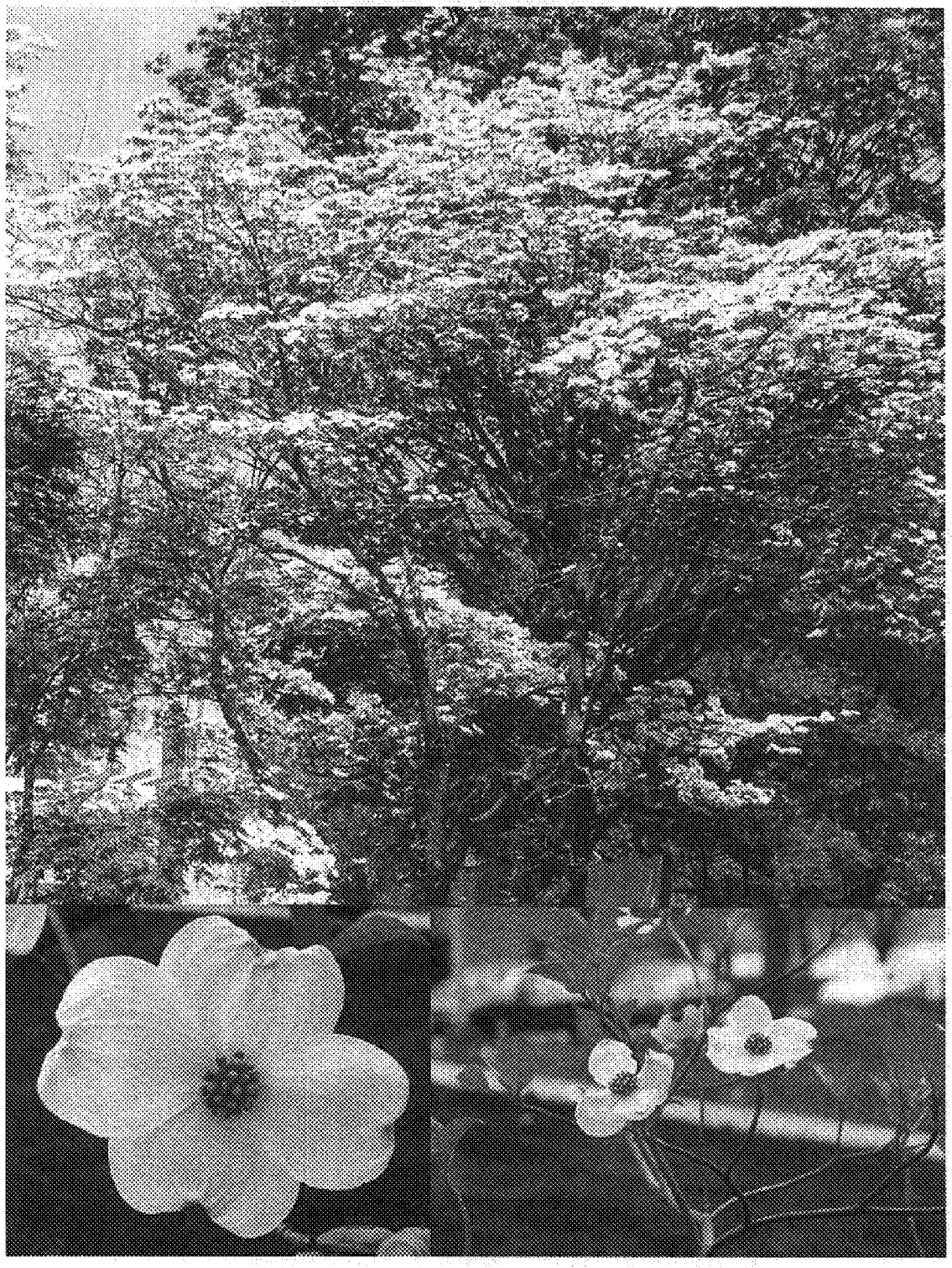
FIG. 1. Photograph of a typical inflorescences of 'Missy's Appalachian Morning' depicting subtending bracts, flower buds and bark characteristics. Inflorescences, flower buds and fall foliage colors in the photograph may differ from the actual colors due to lighting and light reflectance.

'Missy's Appalachian Morning' is a white flowering dogwood cultivar established in the landscape of the University of Tennessee campus in Knoxville, Tenn. This cultivar has been reproduced asexually by rooting cuttings and grafting axillary buds onto seedling rootstock.

'Missy's Appalachian Morning' has white (Green-White Group 157 D: All color classifications are based on The Royal Horticultural Society's Colour Chart) bracts. The upper pair of bracts overlap the lower bracts. The lower pair of bracts average almost 35 mm in length and 42 mm in width. The upper bracts have the dimensions of 35 mm length by 34 mm in width (N=20). The greatest overall width of the inflorescences averages approximately 85 mm (n=20). The clefts at the end of the bracts are Red-Purple (59A) when color is present and may be either flat or pointed. Flower petals are Yellow-green (151B) with Green (134B) sepals and Yellow (2C) anthers. There are about 29 flowers per inflorescence (n=20).

'Missy's Appalachian Morning' is white flowering dogwood, which, to the knowledge of the inventors, is the only cultivar that the seeds will not germinate after standard industry practices of cold/moist stratification for four (4) months. A summary is provided in Table 1 for 1998 through 2003 data collected at the University of Tennessee, Knoxville, Tenn.

TABLE 1

Germination of dogwood seeds.

| Year[a] | 'Missy's Appalachian Morning' | | Other Landscape Dogwoods | |
|---|---|---|---|---|
| 1998/1999 | 0/241[b] | 0% | 375/485 | 77% |
| 1999/2000 | 0/64 | 0% | 251/335 | 75% |
| 2000/2001 | 0/283 | 0% | 463/560 | 83% |
| 2001/2002 | 0/179 | 0% | 198/250 | 80% |
| 2002/2003 | 0/334 | 0% | 267/345 | 77% |
| Totals | 0/1101 | 0% | 1554/1975 | 79% |

[a]Berries were collected in mid-October, depulped and the seeds dried for two days. Seeds were placed in a moist sand/peat mixture and stored at 4C for four months. Germination was assessed one month after placing in the greenhouse (mid-March the following year).
[b]numerator equals the number of seeds that germinated; denominator equals the number of seeds placed in cold.

DNA amplification fingerprinting (DAF) was used to type 'Missy's Appalachian Morning'. The methodology followed that of Trigiano and Caetano-Anolles (HortTechnology, 8:413-423 [1998]). Data, obtained from 144 loci generated from genomic DNA using six (6) arbitrary octomeric primers, were used to compare 'Missy's Appalachian Morning', the subject of his application, to other dogwoods including patented powdery mildew resistant cultivars 'Karen's Appalachian Bush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2) and other commonly found cultivars in nurseries, including *C. florida* 'Plena', which also exhibits white bracts (supernumerary bracts also), but is sterile and *C. florida* 'Cherokee Brave', a red-bracted cultivar. The sequence of the primers were the following (5' to 3'): GAG CCT GT; GAT CGC AG; GTA TCG CC; AAT GCA GC; CTA ACG CC; and GTA ACG CC. DAF as well as cluster analyses were completed using the NTSYS-pc program, version 2.2 (Exeter Software, 100 N. Country Road, Sedtauket, N.T. 11733). A similarity index is provided in FIG. 2 and FIG. 3 which depicts the cluster analysis of the relationship between flowering dogwood cultivars.

Figures 2, 3:
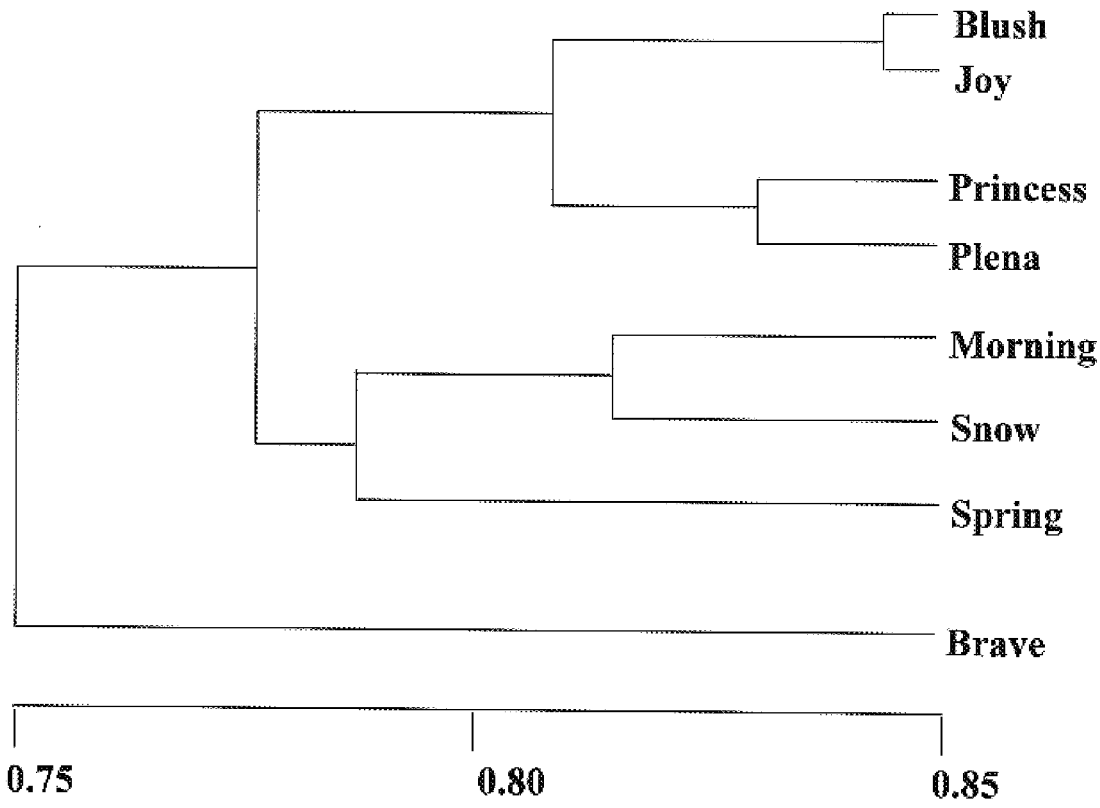
FIG. 2. A similarity index for various dogwoods.
FIG. 3. Cluster analysis of various dogwoods.

The abbreviation found in FIGS. 2 and 3 are as follows: Blush='Karen's Appalachian Blush'; Joy='Appalachian Joy'; Morning='Missy's Appalachian Morning'; Snow='Jean's Appalachian Snow'; Spring='Appalachian Spring'; Brave='Cherokee Brave'; Princess='Cherokee Princess'; and Plena='Plena'. All are white-bracted flowering dogwood cultivars except 'Cherokee Brave', which is red.

DETAILED BOTANICAL DESCRIPTION

The following observations, measurements and comparisons describe this cultivar grown in Knoxville, Tenn. The dogwood used for this description was about 15 days old and was growing in the landscape of The University of Tennessee Agricultural Campus. Plant hardiness is expected to be zones 5–9.

The following descriptions uses color references to The Royal Horticultural Society Colour Chart, except where general terms of ordinary dictionary significance are used. All color ratings were on adaxial surfaces. Ratings for abaxial surfaces were not obtained because reflected/refracted light, due to the density of pubescence on abaxial surfaces, made accurate color determinations difficult or impossible. Measurements are provided as a range with the middle value providing the average (lower limit<average value<upper limit).

Botanical classification: *Cornus florida* L., 'Missy's Appalachian Morning'.

Parentage: Unknown.

Propagation:

*Type.*—Terminal softwood cuttings.

*Time to initiate roots (in June).*—About 3–4 weeks at about 25–30° C.

*Rooting habit.*—Profuse from base of cutting.

*Rooting hormone.*—5,000–10,000 ppm; five (5) second quick dip of DIP 'N' GROW (1% IBA, 0.5% NAA) (Dip 'N' Grow, Inc., Clackamas, Oreg.).

*Intermittent mist.*—Six (6) seconds ever six (6) minutes.

*Light.*—30–50% shade cloth over propagation bench.

*Media.*—Peat-perlite. Axillary bud grafting in mid-August to mid-September onto *Cornus florida* rootstock derived from bulked seed collections.

Plant description:

*Plant form and growth habit.*—Perennial deciduous tree, mostly upright with more or less horizontal branching.

*Plant size.*—A fifteen (15) year-old tree attained the height of about 550 cm and a width of about 155 cm. A four year-old tree from budding attained the height of about 180 cm and a diameter of about 5.5 cm.

*Vigor.*—Similar to other *Cornus florida* cultivars.

*Branching habit.*—Moderate, branch crotch angles of about 20–40° to main trunk.

*Main stem/trunk description.*—Diameter: about 18.5 cm; bark texture: smooth; bark color: Gray-green group (197C).

*Lateral branch description.*—Branch angle of about 45° with a range of 40–52°.

Foliage description:

*Arrangement.*—Simple, opposite; leaves mostly crowded towards branch apices.

*Leaf blade length (cm).*—10.4<10.9<12.2 (n=10).

*Leaf blade width (cm).*—5.2<6.2<7.4 (n=10).

*Petiole length (cm).*—5.2<6.2<7.4 (n=10).

*Petiole diameter (mm).*—About 0.9<1.3<1.7 (n=10).

*Shape.*—Broadly ovate.

*Apex.*—Acuminate, leaf tips mostly flat.

*Base.*—Acute to cuneate, about 5% unequal.

*Margin.*—Entire, slightly undulate.

*Texture.*—Upper surface: nearly glabrous lower surface: leaf hairs profuse on veins and vein axils (u) — 15<25<36.

*Color.*—Yellow-green 144 A.

*Leaf vein arrangement.*—Six (6) pairs, mostly opposite. Petiole reflexed about 80° from the plane of the leaf.

*Bipolar trichomes.*—Upper surface — low density (um) 6<7.2<10 lower surface (um) 6<9.8<14.

Flower description:

*Fragrance.*—None.

*Flower bud size.*—7.3 mm (widest diameter) (n=10). 5.3 mm (base to tip) (n=10).

*Shape of involucral bracts.*—Obovate/pandurate.

*Apex shape of involucral bracts.*—Cuneate.

*Number of bracts.*—4.

*Natural flowering season.*—Typically first through last week in April.

*Inflorescence arrangement.*—The rigid sets of bracts overlap. The outer pair of bracts (closest to the receptacle) are almost square (35 mm in length×34 mm in width) and the inner sets of bracts are wider (42 mm) than they are long (35 mm) (n=20).

*Inflorescence width* (*fully open*).—About 8.5 cm (n=20).

*Bracts*.—Bract dimensions: The outer pair of bracts (closest to the receptacle) are almost square (35 mm in length×34 mm in width) and the inner sets of bracts are wider (42 mm) than they are long (35 mm) (n=20). Bracts are green white (157 D) and clefts are pointed or flat develop and Red-purple (59A). Fully expanded inflorescences are about 85 mm wide. Floral development is asynchronous within the inflorescence. Anthers are Yellow (2C) and average 1.2 mm in length. There are four (4) stamens.

*Sepals*.—The four (4) sepals are Green (134B). The four sepals are fused into an elongated cylinder approximately 2.4 mm in diameter. Individual sepals are entire and smooth culminating into an equal-sided point (acute apex). Each side of the point is approximately 0.8 mm. Each sepal from the base to the tip averages approximately 3.7 mm and is about 1.3 mm wide (n=20).

*Flower number*.—About 29 per inflorescence.

*Petal color*.—Yellow green (151B).

*Ovary*.—Bilocular with each locule have one (1) ovule.

Fruit description:

*Berry type*.—Elliptical drupe (about 14 mm×7 mm) aggregated on the receptacle. Typically, 1 to 11 berries per inflorescence.

*Berry color* (*when ripe in October*).—Deep red (45 A); flesh yellow-orange (22 A).

We claim:

1. A new and distinct cultivar of Dogwood, *Cornus florida* L., named 'MISSY'S APPALACHIAN MORNING', as illustrated and described.

* * * * *

| | Blush | Joy | Morn | Snow | Spring | Brave | Princess | Plena |
|---|---|---|---|---|---|---|---|---|
| Blush | 1.00 | | | | | | | |
| Joy | 0.85 | 1.00 | | | | | | |
| Morn | 0.81 | 0.78 | 1.00 | | | | | |
| Snow | 0.80 | 0.82 | 0.81 | 1.00 | | | | |
| Spring | 0.79 | 0.74 | 0.80 | 0.76 | 1.00 | | | |
| Brave | 0.75 | 0.78 | 0.79 | 0.74 | 0.71 | 1.00 | | |
| Princess | 0.78 | 0.81 | 0.76 | 0.73 | 0.73 | 0.72 | 1.00 | |
| Plena | 0.85 | 0.78 | 0.80 | 0.75 | 0.75 | 0.78 | 0.84 | 1.00 |

UNITED STATES PATENT AND TRADEMARK OFFICE

CERTIFICATE OF CORRECTION

PATENT NO. : PP 18,292 P3
APPLICATION NO. : 11/315886
DATED : December 11, 2007
INVENTOR(S) : Robert N. Trigiano, Mark T. Windham and Alan S. Windham It is certified that error appears in the above-identified patent and that said Letters Patent is hereby corrected as shown below:

Column 1,
Line 26, "typical inflorescences" should read --typical inflorescence--.

Column 3,
Line 7, "of his application" should read --of this application--.
Line 51, "15 days old" should read --15 years old--.

Column 4,
Line 12, "ever six (6) minutes" should read --every six (6) minutes--.
Lines 45-46, "nearly glabrous lower surface" should read --nearly glabrous; lower surface--.
Line 53, "6 < 7.2 < 10 lower surface" should read --6 < 7.2 < 10; lower surface--.

Column 5,
Line 9, "green white" should read --green-white--.

Signed and Sealed this

Seventeenth Day of June, 2008

JON W. DUDAS
*Director of the United States Patent and Trademark Office*